United States Patent
Spoor et al.

(10) Patent No.: US 11,287,672 B2
(45) Date of Patent: Mar. 29, 2022

(54) OPHTHALMIC DEVICE FORMED BY ADDITIVE FABRICATION AND METHOD THEREOF

(71) Applicant: Additive Ophthalmic Optics, LLC, Macedon, NY (US)

(72) Inventors: Ronald Spoor, Penn Yan, NY (US); Sanjay M. Rastogi, Kalamazoo, MI (US); Charles P. Henning, Fairport, NY (US)

(73) Assignee: Additive Ophthalmic Optics, LLC, Macedon, NY (US)

( * ) Notice: Subject to any disclaimer, the term of this patent is extended or adjusted under 35 U.S.C. 154(b) by 372 days.

(21) Appl. No.: 16/109,160

(22) Filed: Aug. 22, 2018

(65) Prior Publication Data

US 2018/0364499 A1   Dec. 20, 2018

Related U.S. Application Data

(63) Continuation of application No. 14/578,887, filed on Dec. 22, 2014, now Pat. No. 10,139,651, which is a continuation of application No. 12/341,067, filed on Dec. 22, 2008, now Pat. No. 8,940,219.

(60) Provisional application No. 61/018,009, filed on Dec. 31, 2007.

(51) Int. Cl.

| | |
|---|---|
| *G02C 7/04* | (2006.01) |
| *A61F 2/16* | (2006.01) |
| *B29D 11/00* | (2006.01) |
| *G02C 7/02* | (2006.01) |
| *B33Y 10/00* | (2015.01) |
| *B33Y 80/00* | (2015.01) |

(52) U.S. Cl.
CPC .......... *G02C 7/04* (2013.01); *A61F 2/16* (2013.01); *B29D 11/00038* (2013.01); *B29D 11/0073* (2013.01); *G02C 7/022* (2013.01); *G02C 7/049* (2013.01); *A61F 2240/001* (2013.01); *B33Y 10/00* (2014.12); *B33Y 80/00* (2014.12); *G02C 2202/16* (2013.01)

(58) Field of Classification Search
CPC .......... G02C 7/04; G02C 7/022; G02C 7/049; G02C 2202/16; A61F 2/16; A61F 2240/001; B29D 11/00038; B29D 11/0073; B33Y 10/00; B33Y 80/00
USPC ....................................................... 427/2.1
See application file for complete search history.

(56) References Cited

U.S. PATENT DOCUMENTS

| | | | | |
|---|---|---|---|---|
| 2003/0035917 A1* | 2/2003 | Hyman | ............. | B41M 5/36 428/67 |
| 2005/0012998 A1* | 1/2005 | Kumar | ............. | C07D 311/94 359/487.02 |

* cited by examiner

*Primary Examiner* — Ling Siu Choi
*Assistant Examiner* — Ronald Grinsted
(74) *Attorney, Agent, or Firm* — Brian B. Shaw, Esq.; Harter Secrest & Emery LLP

(57) ABSTRACT

An ophthalmic device is formed by additive fabrication, the optical device having an optical surface with a surface roughness on the order of less than 10 microns. A method is provided for making an ophthalmic device including an optical surface having a surface roughness of less than 10 microns by depositing on a stage in a first relative position a first lamina of particulates having a size less than 10 microns and in select configurations less than two microns and certain configurations less than one micron, and, synergistically stimulating the first lamina of particulates to form a first solidified layer.

12 Claims, 4 Drawing Sheets

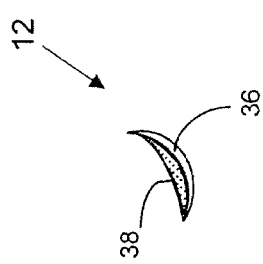
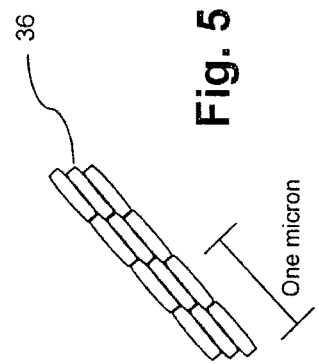

OPHTHALMIC DEVICE FORMED BY ADDITIVE FABRICATION AND METHOD THEREOF

CROSS-REFERENCE TO RELATED APPLICATIONS

The present application is a continuing application of U.S. Ser. No. 12/341,067 filed Dec. 22, 2008 which claims the benefit of U.S. provisional patent application 61/018,009 filed Dec. 31, 2007, the disclosure of each of which is hereby expressly incorporated by reference.

STATEMENT REGARDING FEDERALLY SPONSORED RESEARCH OR DEVELOPMENT

Not applicable.

REFERENCE TO A "SEQUENCE LISTING"

Not applicable.

TECHNICAL FIELD

This invention relates to the formation of three dimensional objects using additive fabrication techniques. More specifically, the invention relates to an ophthalmic device which is formed by additive fabrication and a method of making the same.

BACKGROUND OF THE INVENTION

Three dimensional objects can be made rapidly and automatically by rapid prototyping and manufacturing (RP&M). RP&M has proven to be a cost effective technique used to develop prototypes and to manufacture various three dimensional products. RP&M is usually classified according to specific techniques. Each technique is discussed seriatim below.

A first known technique for making three dimensional objects is by applying successive layers of unsolidified, fluid-like material to a working surface. The layers are then selectively solidified according to cross-sectional computer data representing the object. These solidified layers, or laminae, are typically formed of a photo polymer liquid material and solidified via visible or ultraviolet electromagnetic radiation from a laser. More specifically, his technique involves applying liquid material to areas which will, and which will not, be part of the finished three dimensional object. The radiation is then used to solidify only those areas that are part of the three dimensional object. Often referred to as stereolithography, this technique is known and disclosed in several patents and patent applications, for example, U.S. Pat. No. 4,575,330 to Hull. Similarly, layers of a powered material can be selectively solidified by depositing a chemical binder material thereon.

Another type of RP&M is selective deposition modeling, which creates three dimensional objects by selectively depositing a liquid like material onto a working surface in patterns that become part of a solidified layer. That is, a layer is deposited based on cross-sectional data that represents slices of the three-dimensional object and is then solidified. A subsequent layer is added and solidified to the previously formed solidified layer. By repeating these steps, a three dimensional object is built lamina-by-lamina. With this technique, the liquid material is flowable but only deposited in the regions that form the three dimensional object.

Yet a third technique used for RP&M is laminated object manufacturing. With this method, three dimensional objects are formed by stacking sheets of material together wherein each sheet is adhered to another. The stacked sheets are then selectively cut in a particular order to form the desired three dimensional object, according to computer data representing the cross-sectional slices of the three dimensional object.

While these techniques have allowed for the manufacturing of many different types of three dimensional objects, they have not been useful in the creation of ophthalmic devices. Heretofore, the RP&M techniques described above have only achieved surface variations of the object of approximately 50 microns or greater.

SUMMARY OF THE INVENTION

Ophthalmic devices require a surface variation or roughness in the optical surface that is less than approximately 10 microns and typically less than two microns and preferably less than one micron. An extreme topography of the optical surface as in the prior art, such as on the order of 50 microns, causes discrepancies in the refractive indices as a result of the "hills" and "valleys" in the optical surface.

It is therefore, desirable to provide an ophthalmic device using additive formation techniques, wherein the ophthalmic device has a surface variation or roughness on the order of less than 10 microns and in select configurations less than two microns and in certain configurations less than one micron (submicron).

The present disclosure broadly comprises an ophthalmic device having an optical surface formed by additive fabrication, wherein the optical surface has a surface roughness of less than 10 microns, and in select configurations less than 2 microns, and preferably less than one micron.

The present disclosure further comprises a method of making an ophthalmic device having an optical surface by depositing on a stage in a first relative position a first lamina of particulates having a size less than 10 microns and in select configurations less than 2 microns and in certain configurations less than one micron, and synergistically stimulating the first lamina of particulates to form a first solidified layer, a portion of the layer forming a portion of the optical surface.

The present disclosure further comprises an ophthalmic device and method of making such an ophthalmic device having an optical surface by depositing on a stage in a first relative position a first lamina having a thickness of less than 10 microns and in select configurations less than 2 microns and in certain configurations less than one micron, and, synergistically stimulating the first lamina of particulates to form a first solidified layer, the layer forming at least a portion of the optical surface. The resulting optical surface can have a surface roughness less than 10 microns and in select configurations less than 2 microns and in certain configurations less than one micron.

The present disclosure also comprises a method of forming an ophthalmic device comprising depositing by additive fabrication a plurality of bonded laminae to define an optical surface, the lamina having a thickness of less than 10 microns, and in select configurations less than 2 microns and in certain configurations less than one micron.

An object of the disclosure is to provide an ophthalmic device having an optical surface with surface roughness less than 10 microns, and in select configurations less than 2 microns and in certain configurations less than one micron, the optical surface formed by additive fabrication.

It is another object of the disclosure to provide an ophthalmic device having an optical surface formed from solidified layers of particulates, the particles having a size less than 10 microns, and in select configurations less than 2 microns and in certain configurations less than one micron.

It is further object of the invention to provide a method of making an ophthalmic device by additive fabrication, wherein the ophthalmic device has an optical surface with a surface roughness of less than 10 microns, and in select configurations less than 2 microns and in certain configurations less than one micron.

The novel aspects of the invention are set forth with particularity in the appended claims. The invention itself, together with further objects and advantages thereof, may be more readily comprehended by reference to the following detailed description of a presently preferred embodiment of the invention taken in conjunction with the accompanying drawings.

BRIEF DESCRIPTION OF THE DRAWING FIGURES

FIG. 4 is a perspective view of laminae of an ophthalmic device.

FIG. 5 is a partial cross-sectional view of an ophthalmic device.

DETAILED DESCRIPTION OF THE INVENTION

At the outset, it should be appreciated that the use of the same reference number throughout the several figures designates a like or similar element.

Figure 1:
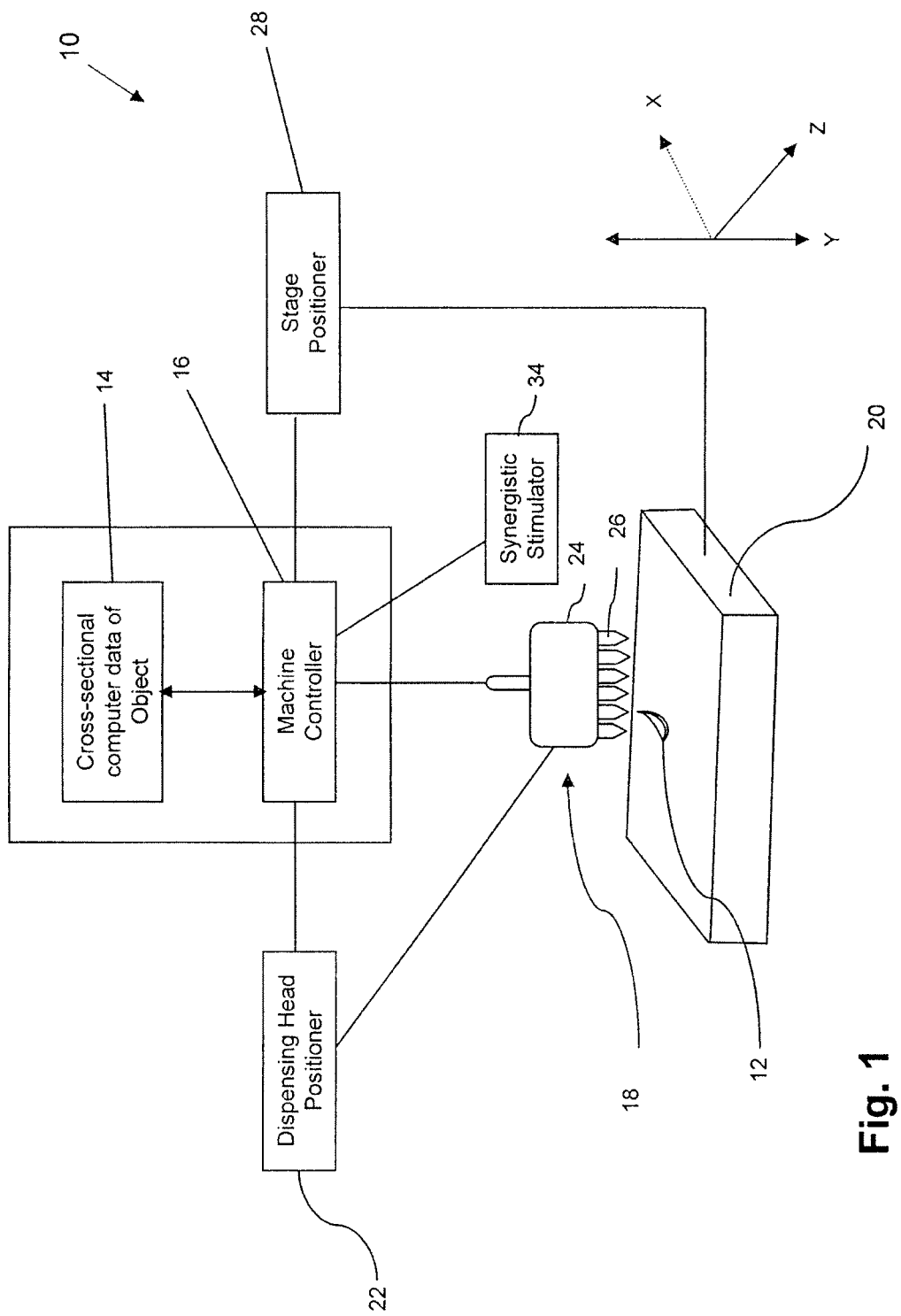
FIG. 1 is a schematic diagram of main functional components of an additive fabrication apparatus.
Figure 2:
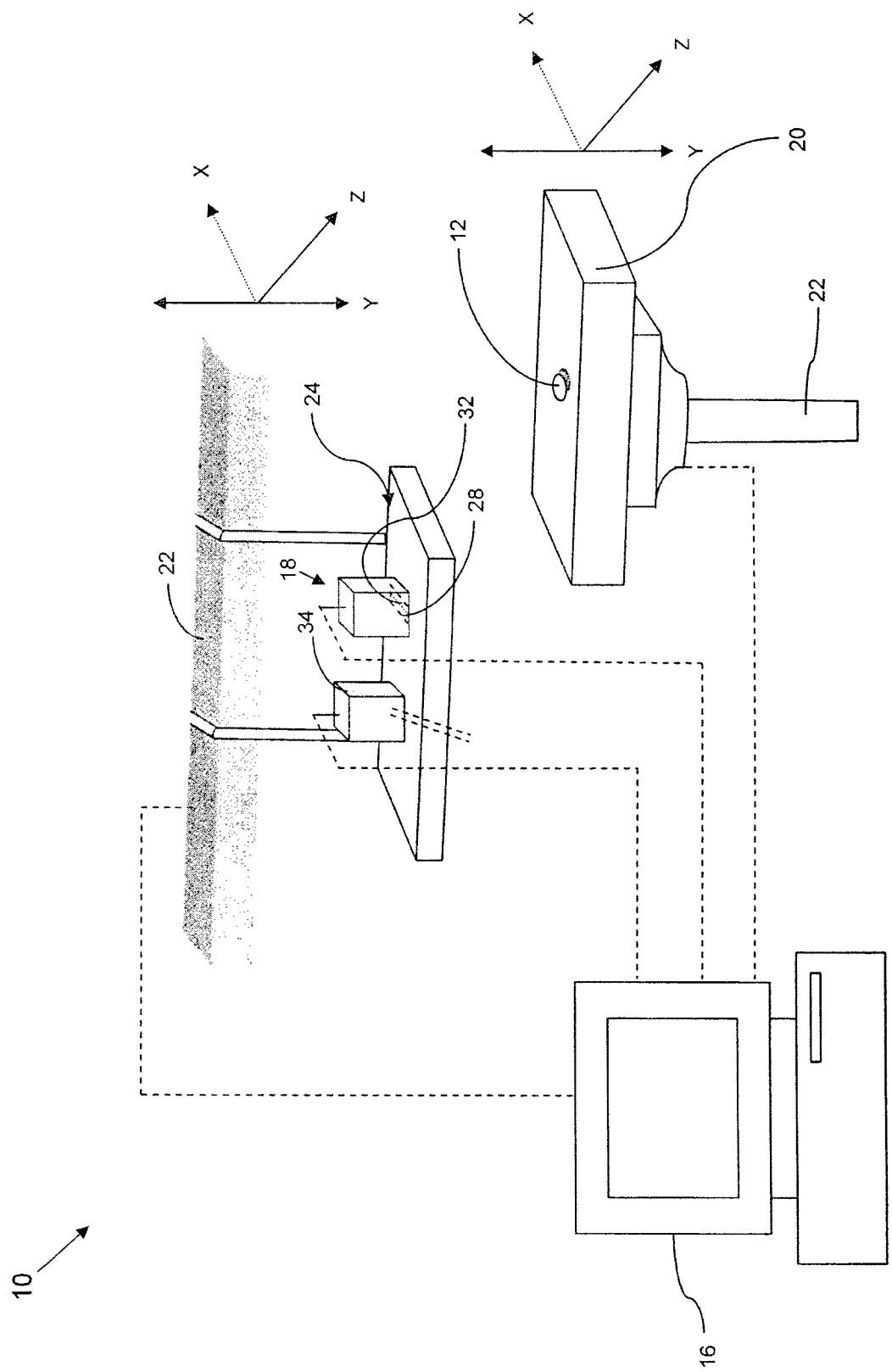
FIG. 2 is a perspective view of the main functional components of the additive fabrication apparatus.
Figure 3:
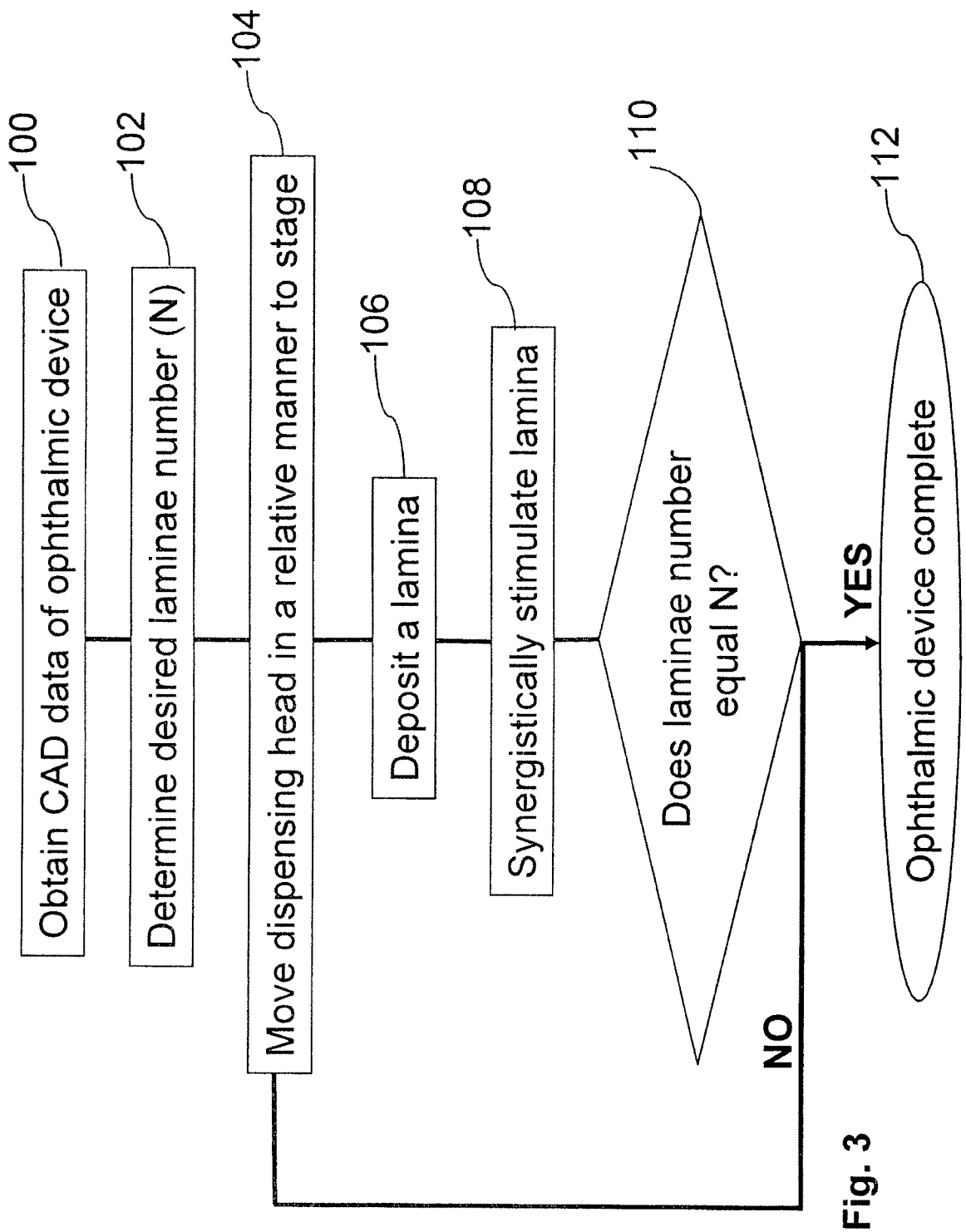
FIG. 3 is a flow chart diagram illustrating the build-up of the ophthalmic device of FIG. 1.

Referring now to the Figures, FIGS. 1 and 2 depict a schematic representation of an additive fabrication apparatus 10 for use in making ophthalmic devices 12. In one configuration, the additive fabrication apparatus 10 includes cross-sectional computer data 14 of a three-dimensional object which is transferred to a computer system comprising a machine controller 16. The cross-sectional computer data 14 can be created in a typical computer aided design (CAD) system, wherein a user creates an ophthalmic device which can be saved as a data file containing coordinate information corresponding to cross-sectional slices of the ophthalmic device 12. Such method and apparatus for slicing a three-dimensional object is described in U.S. Pat. No. 5,854,748 to Snead et al., which is hereby incorporated by reference. This data file of the ophthalmic device 12 is formed into coded binary information that is transferred to a machine controller 16.

The machine controller 16 communicates with a dispensing head 18 and a stage 20 arranged to support the ophthalmic device 12 being formed. The dispensing head 18 is connected to a dispensing head positioner 22, wherein the dispensing head 18 is selectively moveable in the X- and Y-axes by commands from the machine controller 16. In an embodiment of the invention, the dispensing head 18 is also selectively moveable in the Z-axis. More preferably, the dispensing head 18 is moveable in any direction according to instructions received from the machine controller 16.

The dispensing head 18 undergoes back and forth movements and accelerations, similar to commercial print head configurations used in typical three-dimensional modeling systems. The dispensing head 18 may be any suitable ejection head having an ejection nozzle 24 for emitting small mass particulates or droplets of particulate material. In one embodiment the dispensing head 18 ejects droplets that are less than 10 microns and in select configurations less than two microns and certain configurations less than one micron (submicron) in size. In one embodiment, the dispensing head 18 comprises an array of dispensing pins 26 arranged in the nozzle 24 which dispense a plurality of particulates according to the instructions received from the machine controller 16. Each dispensing pin 26 is individually controllable such that particulates may be dispensed from some, but not all of the pins 26, according to the machine controller 16 instructions. Any suitable number of dispensing pins 26 may be utilized. Further, the pins 26 may be configured according to any preferred arrangement. The dispensing head 18 can be configured similar to the droplet dispenser disclosed in U.S. Pat. No. 6,808,683 to Gilbert, which is hereby incorporated by reference. Alternatively, the nozzle 24 may include orifices 28 capable of dispensing micron or submicron sized particulates as discussed in more detail below, wherein any optimal number of orifices 28 can be selected and arranged in a desired configuration.

In an embodiment, the particulates are formed from unsolidified, flowable material which is curable, for example, thermoplastic, monomeric or wax-like material. The ejected material for forming the ophthalmic device can be as set forth in the following US patents, each of which is hereby expressly incorporated by reference, U.S. Pat. No. 7,297,160 entitled High refractive-index, hydrophilic, arylsiloxy-containing macromonomers and polymers, and ophthalmic devices comprising such polymers; U.S. Pat. No. 7,279,538 entitled Aromatic-based polysiloxane prepolymers and ophthalmic devices produced therefrom; U.S. Pat. No. 7,198,639 entitled Polysilsesquioxane containing polymeric compositions; U.S. Pat. No. 7,176,268 entitled Prepolymers for improved surface modification of contact lenses; U.S. Pat. No. 7,169,874 entitled High refractive index polymeric siloxysilane compositions; U.S. Pat. No. 7,138,440 entitled High refractive index polymeric siloxysilane compositions; U.S. Pat. No. 7,132,494 entitled High refractive index aromatic-based silyl monomers; U.S. Pat. No. 7,132,493 entitled High refractive index aromatic-based prepolymer precursors; U.S. Pat. No. 7,132,492 entitled High refractive index aromatic-based prepolymer precursors; U.S. Pat. No. 7,101,949 entitled High refractive index polymeric siloxysilane compositions; U.S. Pat. No. 7,091,299 entitled High refractive index polymeric siloxysilane compositions; U.S. Pat. No. 7,009,024 entitled High refractive index aromatic-based siloxane difunctional macromonomers; U.S. Pat. No. 7,009,023 entitled High refractive index aromatic-based siloxane difunctional macromonomers; U.S. Pat. No. 7,005,494 entitled High refractive index aromatic-based siloxane monofunctional macromonomers; U.S. Pat. No. 6,992,162 entitled High refractive index aromatic-based siloxane monofunctional macromonomers; U.S. Pat. No. 6,989,430 entitled High refractive index aromatic-based siloxane monofunctional macromonomers; U.S. Pat. No. 6,956,087 entitled High refractive index polysiloxane prepolymers; U.S. Pat. No. 6,951,914 entitled High refractive index aromatic-based prepolymer precursors; U.S. Pat. No. 6,908,978 entitled High refractive index polymeric siloxysilane compositions; U.S. Pat. No. 6,906,162 entitled High refractive index aromatic-based siloxane monofunctional macromonomers; U.S. Pat. No. 6,891,010 entitled Silicone hydrogels based on vinyl carbonate endcapped fluorinated side chain polysiloxanes; U.S. Pat. No. 6,881,809 entitled High refractive index aromatic-based silyl monomers; U.S. Pat. No. 6,881,808 entitled High refractive index aromatic-based siloxane difunctional macromonomers; U.S. Pat. No. 6,864,342 entitled High refractive index aromatic-based prepolymers and U.S. Pat. No. 6,864,341 entitled High refractive index aromatic-based prepolymer precursors.

In an alternative embodiment, the particulates are a chemical binder which adhere material in a powdered form. Of course, if a chemical binder and particulate embodiment is used, the refractive index of each material should be approximately the same, and more preferably identical.

The dispensing head 18 utilizing orifices 28 capable of dispensing micron or submicron sized particulates, preferably includes an orifice plate 32 mounted on the dispensing portion of the dispensing head 18. Each orifice 28 is preferably equipped with a piezoelectric element that causes a pressure wave to propagate through the material when an electronic firing pulse is supplied to the element. The pressure wave causes the particulate material to be released from the orifice 28. The machine controller 16 determines the rate and timing of the firing pulse applied to each individual orifice 28.

To accurately build the ophthalmic device 12, the particulates dispensed from the dispensing head 18 need to be accurately placed in a desired location so that the particulate layers, or laminae, can be built-up vertically. The desired location is determined from the computer data providing a data map or pixel locations that identify the desired location. To obtain such desired location, the dispensing head 18 must be directed to a predetermined dispensing position by the dispensing head positioner 22. Additionally, the stage 20 for supporting the ophthalmic device 12 can be directed to a predetermined stage position by a stage positioner 30, wherein the stage position is related to the predetermined dispensing position at the particular time of firing of the material through the ejection nozzle 24. The stage 20, connected to the stage positioner 30, is selectively moveable in the X and Y-axes by commands from the machine controller 16. That is, in an embodiment of the invention, the stage 20 is moveable, horizontally and perpendicularly to the ground. In an embodiment of the invention, the stage 20 is also selectively moveable in the Z-axis. Although the stage 20 is preferably moveable along at least the Y-axis, movement of the stage 20 is not required at all since the dispensing head 18 can be moveable in all directions in a relative manner to the stage 20.

The machine controller 16 selectively moves the stage 20 with micron or submicron motion control. Obtaining micron or submicron positioning of a stage in a high resolution system is well known in the art and can be performed by commercially available or custom developed systems such as the DynamYX and the Mat350 submicron positioning systems of Kensington Laboratories of Richmond, Calif., the nano resolution linear stages of ALIO Industries of Wheat Ridge, Colo., the motion controllers and the NanoStepper of Baldor Electric Company of Fort Smith, Ark., the multi-axes, sub-micron positioner described in U.S. Pat. No. 6,888,289 to Heilig et al. which is hereby incorporated by reference, and the motion controllers of Galli Motion Control, Inc.

In one embodiment, raster scanning is used to position the dispensing head 18 having either pins 26 or orifices 28 at the desired firing locations. That is, the printing process for each lamina is accomplished by a series of relative movements between the dispensing head 18 and the desired firing locations. Printing typically occurs as the dispensing head 18 relatively moves in a main scanning direction. This is followed by a typically smaller increment of movement in a secondary scanning direction while no dispensing occurs, which in turn is followed by a reverse scan in the main scanning direction in which dispensing again occurs. The process of altering main scans and secondary scans occurs repeatedly until the laminae are completely deposited.

Alternative embodiments may perform small secondary scanning movements while main scanning occurs. Because of the typically large difference in net scanning speed along the main and secondary directions, such an alternative still results in deposition along scanning lines which are nearly parallel to the main scanning direction and perpendicular to the secondary scanning direction. Further alternative preferred embodiments may utilize vector scanning techniques or a combination of vector scanning and raster scanning techniques.

The liquid particulates, immediately after being dispensed from the dispensing head 18, have an elongated shape, compared to the width of the particulates. The ratio of particulate length to width can be defined as the aspect ratio of the particulate. The aspect ratio of these particulates becomes smaller as the particulates travel away from the dispensing head 18. Nonetheless, the spacing between the dispensing head 18 and stage 20 is minimized to avoid inaccurate deposition, since inaccuracies increase with the distance the particulates travel.

The additive fabrication apparatus 10 further includes a synergistic stimulator 34 that causes the particulates dispensed from the dispensing head 22 to selectively harden. In one embodiment, the synergistic stimulator 34 is a ultraviolet (UV) laser which is capable of curing a liquid material. Alternatively, the synergistic stimulator 34 can be infrared (IR) radiation from a carbon dioxide laser, which can selectively harden a sinterable powered. Further, the synergistic stimulator 34 can be a chemical binder which can adhere particulate powder upon selective application of the chemical binder. It should be appreciated by those having ordinary skill in the art that, the synergistic stimulation can be applied after the liquid material is fully deposited on the stage 20, wherein the synergistic stimulation defines areas that will be part of the ophthalmic device 12. Alternatively, the synergistic stimulation can be applied lamina-by-lamina, wherein material is only deposited in areas that form the ophthalmic device 12. Preferably, however, the synergistic stimulation is applied lamina-by-lamina, wherein a layer of material is printed and cured before a next layer is built.

For example, the additive fabrication apparatus 10 builds an ophthalmic device 12 lamina-by-lamina to form an ophthalmic device 12 having an optical surface 36 shown in FIG. 4, wherein the lamina have a thickness less than 10 microns and in select configurations less than two microns and certain configurations less than one micron (submicron) in size. "Ophthalmic device" is meant to include, but is not limited to, a device suitable for placement in the eye, for example, an intraocular lens (IOL) or a corrective, therapeutic or cosmetic contact lens. The optical surface 36 of the ophthalmic device 12 has a surface roughness of less than 10 microns and in select configurations less than two microns and certain configurations less than one micron (submicron) in size. That is, the surface topography of the ophthalmic device 12 can have a surface roughness of less than one micron.

As shown in the figures, to build an ophthalmic device, a desired number of laminae is determined (step 102) based on information obtained from the CAD data (step 100). The stage 20 and/or the dispensing head 18 are directed to move by the machine controller 16 (step 104) and a lamina is dispensed (step 106). When the first lamina is being dispensed, the nozzle 24 is arranged in a predetermined position in relation to the stage 20. The last-built lamina is positioned proximate to the nozzle 24 allowing the next to-be-built lamina to be placed in a registered manner with the first lamina. The nozzle 24 undergoes back and forth movements and accelerations until a new lamina is deposited on the last-built lamina. During the translation of the dispensing head nozzle 24, the particulates are ejected therefrom. A sacrificial material 38 can be used to support the laminae during the printing process. That is, to prevent the laminae from collapsing during formation, a wax-like material can be simultaneously or contemporaneously ejected from some of the orifices 28 or pins 26 of the nozzle 24.

Once a lamina is formed, the synergistic stimulator 34 selectively hardens the lamina (step 108). In a preferred embodiment, UV radiation is used to cure the lamina. As discussed above, however, other synergistic stimulators can be used. For example, the synergistic stimulator 34 can be a chemical binder ejected from the dispensing head 18 to adhere a powdered material. The machine controller 16 determines whether the desired laminae number has been reached upon completion of the lamina deposit (step 110). If not, the next lamina is formed in a registered manner with respect to the last-built lamina, wherein the dispensing head 18 and/or stage 20 are translated to align the dispensing head 18 with respect to the last built lamina. This process of lamina depositing and synergistic stimulation is repeated until the desired number of laminae has been completed (step 112).

The ophthalmic device 12 oriented in a convex position can be built by depositing a first lamina ring having a predetermined circumference of particulate material and then applying additional, progressively smaller lamina rings of particulate material to the last-build laminae. Sacrificial material 38 can be deposited in the enclosed regions to support the laminae. The ophthalmic device 12 oriented in a concave position can be created by depositing progressively larger lamina rings having a predetermined circumference on the last-built lamina, wherein sacrificial material 38 is deposited on the outer surface of the device 12 to support the layers. It should be appreciated that sacrificial material 38 serves several purposes. Specifically, the sacrificial material 38 forms a working surface on which to build object lamina and even successive support lamina. Further, the sacrificial material 38 is easily removable from the optical surface 36 it supports. Also, when removed, only a minimal amount of damage to the optical surface 36 is incurred, which can be corrected by heat annealing as described in more detail below. To optimize building speed, vertical accumulation of the sacrificial material 38 is important and, as such, it is desirable to have sacrificial material 38 built-up at approximately the same rate as the ophthalmic device 12. Specifically, it is preferred that the vertical accumulation of the sacrificial material 38 accumulates at least as fast as the laminae defining the optical surface 36.

It should be apparent that, after the formation of the ophthalmic device 12 using the additive fabrication method described above, an additional optional step can be taken to assist in forming the desired micron or submicron optical surface roughness. That is, the ophthalmic device 12 can be heat annealed, thereby providing a resultant optical surface 36 having a surface roughness of one micron or less than one micron. This step is particularly useful when the optical surface 36 is damaged during the removal of sacrificial material 38.

The surface roughness of the ophthalmic device is a measure of amplitude of surface variations based on the vertical deviations of the roughness profile from a mean line. For example, Ra is the arithmetic average of the absolute values. Thus, in one configuration the surface roughness can be defined as having an Ra of less than 10 microns and in select configurations less than two microns and certain configurations less than one micron (submicron). Alternatively, the surface roughness can be defined in terms of RMS (root mean square) as less than 10 microns and in select configurations less than two microns and certain configurations less than one micron (submicron). Surface finish, surface roughness, is usually specified based on the ASME Y14.36M-1996 standard.

There has thus been described an ophthalmic device formed by additive fabrication having an optical surface with an optical surface having a surface roughness of less than 10 microns and in select configurations less than two microns and certain configurations less than one micron (submicron) and a method of making the same. Those skilled in the art will recognize that modifications may be made in the method and apparatus described herein without departing from the true spirit and scope of the invention which accordingly are intended to be limited solely by the appended claims.

The invention claimed is:

1. An ophthalmic device having an optical surface and a plurality of additive fabrication lamina, wherein one of the plurality of additive fabrication lamina forms at least a portion of the optical surface.

2. The ophthalmic device of claim 1 wherein each of the plurality of additive fabrication lamina is a UV curable material.

3. The ophthalmic device of claim 1 wherein each of the plurality of additive fabrication lamina is an IR curable material.

4. The ophthalmic device of claim 1 further comprising a chemical binder.

5. The ophthalmic device of claim 1 further comprising a removable sacrificial material arranged to support the optical surface.

6. The ophthalmic device of claim 5 wherein the removable sacrificial material is a wax.

7. The ophthalmic device of claim 1 wherein each of the plurality of additive fabrication lamina has a thickness of less than 1 micron.

8. The ophthalmic device of claim 1 wherein the ophthalmic device is a lens.

9. The ophthalmic device of claim 1 wherein the ophthalmic device is a corrective lens.

10. The ophthalmic device of claim 1 wherein the plurality of additive fabrication lamina are printed.

11. A corrective lens consisting of a plurality of printed layers, wherein at least one of the plurality of printed layers forms at least a portion of an optical surface of the corrective lens.

12. An ophthalmic device having an optical surface, the ophthalmic device consisting of a plurality of additive fabrication lamina, wherein one of the plurality of additive fabrication lamina forms at least a portion of the optical surface.

* * * * *